(12) United States Patent
Hearne

(10) Patent No.: US 7,563,256 B2
(45) Date of Patent: Jul. 21, 2009

(54) CANNULA TIP EYE DROP DISPENSER

(76) Inventor: Isaac Hearne, 1697 Trail Head Dr., Reno, NV (US) 89521

(*) Notice: Subject to any disclaimer, the term of this patent is extended or adjusted under 35 U.S.C. 154(b) by 366 days.

(21) Appl. No.: 11/395,045

(22) Filed: Mar. 30, 2006

(65) Prior Publication Data

US 2007/0233020 A1 Oct. 4, 2007

(51) Int. Cl.
*A61M 35/00* (2006.01)
*A61H 35/02* (2006.01)

(52) U.S. Cl. ..................... 604/300; 604/411
(58) Field of Classification Search ................ 604/295, 604/300, 301, 302, 411, 414
See application file for complete search history.

(56) References Cited

U.S. PATENT DOCUMENTS

| | | | | |
|---|---|---|---|---|
| 2,249,832 A * | 7/1941 | Hubschman | .................. | 222/420 |
| 2,382,771 A * | 8/1945 | Bowers | .................. | 604/300 |
| 2,707,469 A * | 5/1955 | Feinstein | .................. | 604/295 |
| 2,736,316 A * | 2/1956 | Stovall | .................. | 604/300 |
| 2,757,671 A * | 8/1956 | Haafkens | .................. | 604/200 |
| 2,802,448 A * | 8/1957 | Young | .................. | 401/134 |
| 2,898,911 A * | 8/1959 | Taylor | .................. | 604/301 |
| 3,244,173 A * | 4/1966 | Berg | .................. | 604/192 |
| 3,592,245 A * | 7/1971 | Schneller e tal. | .................. | 141/25 |
| 3,940,003 A * | 2/1976 | Larson | .................. | 215/247 |
| 4,085,750 A * | 4/1978 | Bosshold | .................. | 604/302 |
| 4,411,661 A * | 10/1983 | Kersten | .................. | 604/411 |
| 4,733,802 A * | 3/1988 | Sheldon | .................. | 604/302 |
| 4,779,768 A * | 10/1988 | St. Amand | .................. | 222/209 |
| 4,927,062 A * | 5/1990 | Walsh | .................. | 222/420 |
| 5,007,905 A * | 4/1991 | Bauer | .................. | 604/295 |
| 5,085,651 A * | 2/1992 | Py | .................. | 604/298 |
| 5,624,057 A * | 4/1997 | Lifshey | .................. | 222/212 |
| 6,105,828 A * | 8/2000 | Kanner et al. | .................. | 222/212 |
| 6,422,433 B2 * | 7/2002 | Evans et al. | .................. | 222/548 |
| 6,558,365 B2 * | 5/2003 | Zinger et al. | .................. | 604/410 |
| 6,571,971 B1 * | 6/2003 | Weiler | .................. | 215/247 |
| 2004/0140319 A1 * | 7/2004 | Gerondale | .................. | 222/1 |
| 2004/0182814 A1 * | 9/2004 | Suffa | .................. | 215/216 |
| 2004/0210203 A1 * | 10/2004 | Kusu et al. | .................. | 604/295 |
| 2005/0274744 A1 * | 12/2005 | Spada et al. | .................. | 222/240 |
| 2006/0081726 A1 * | 4/2006 | Gerondale | .................. | 239/590 |
| 2006/0116649 A1 * | 6/2006 | Hagele | .................. | 604/295 |

* cited by examiner

*Primary Examiner*—Tatyana Zalukaeva
*Assistant Examiner*—Paula L Craig
(74) *Attorney, Agent, or Firm*—Richard D. Clarke

(57) ABSTRACT

The present invention involves an eye drop dispenser attachment having a cannula tip that can provide a consistent dose of medication. The attachment includes a base portion, a neck portion, and a tip portion. The base portion can contain threads for removable attachment to a bottle. The attachment can also include a protective covering for surrounding the tip to prevent injury to a user. The attachment can further include a cap that can be removably attached to either the base portion or the neck portion. The attachment can be incorporated into a bottle assembly or it can be screwed onto an existing bottle. The tip preferably has dimensions consistent with current ophthalmic cannula technology in the range of 20-40 gauge depending on the size of drop desired. An alternate embodiment of the attachment can be slidably disposed on the end of a traditional bulb-type eye dropper.

12 Claims, 5 Drawing Sheets

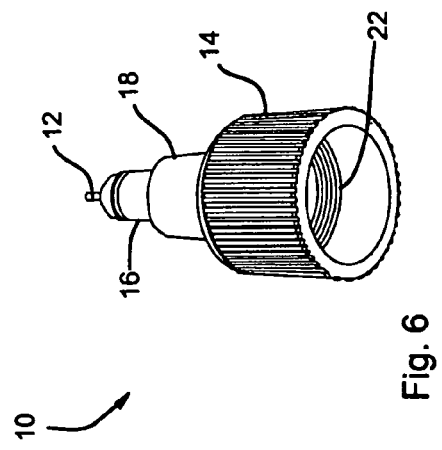
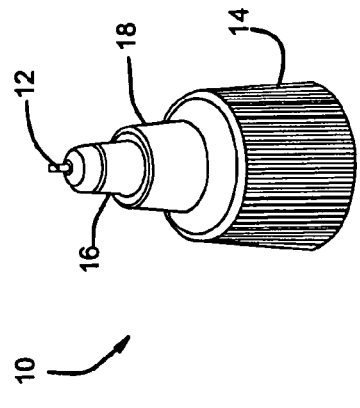
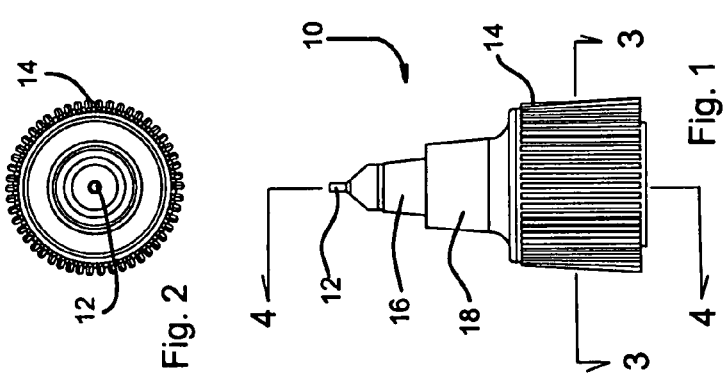
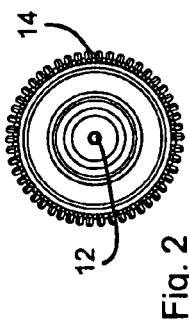
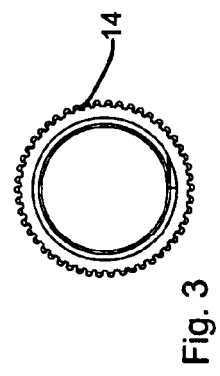
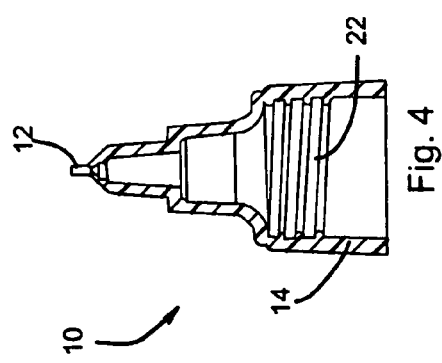

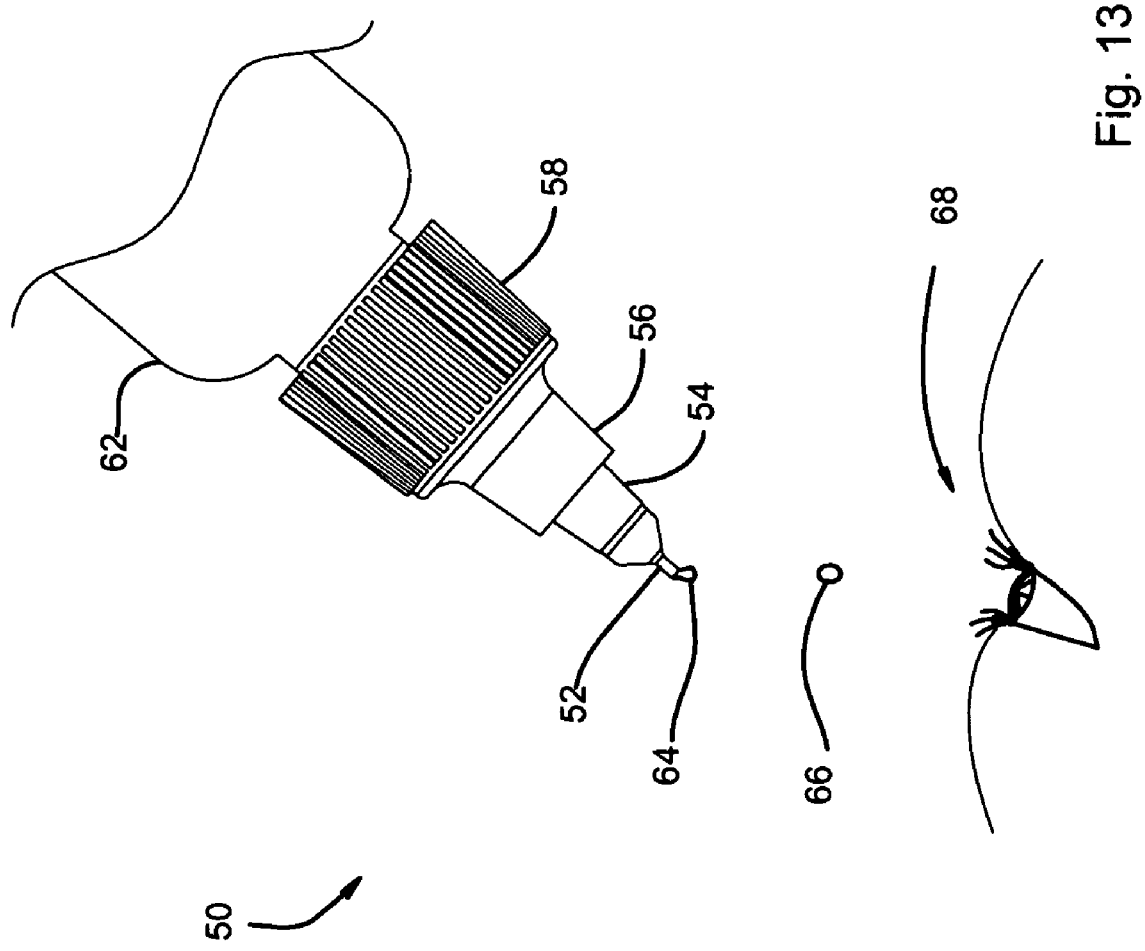

CANNULA TIP EYE DROP DISPENSER

BACKGROUND OF THE INVENTION

1. Field of the Invention

The present invention generally relates to the field of liquid drop delivery devices. More specifically, this patent deals with a smaller yet equally therapeutic medical eye drop device primarily used in delivering consistent, smaller, uniform drops associated with the proper dose of what is being dispensed.

2. Description of the Related Art

Many dispensers discuss improved ways of making eye drop dispensers, enhancing eye drop delivery, facilitating patient self delivery of a smaller yet equally therapeutic medical eye drop. None, however, address the delivery of a smaller yet equally therapeutic medical eye drop.

Currently, almost all eye drop dispensers for human and veterinarian use have roughly the same dimensions. As such, a molded part compatible with one bottle would be compatible with almost all commercially available bottle types. Existing eye drop dispensers produce drops that are roughly 50 micro liters (µl) in size. Only 7-10 (µl) of this amount actually remains in the eye according to the American Academy of Opthalmology Basic and Clinical Science Course. The rest is lost, mainly through tearing. As a result, only about 20% of each drop is therapeutic. The rest is wasted. Therefore applying a tip that will dispense a smaller size eye drop (i.e. 7 µl-25 µl) would minimize waste without sacrificing therapeutic efficacy. This invention is not for a single sized tip. Different sized cannula tips produce different sized drops. The size of which will be optimized to each therapeutic regimen as is necessary.

SUMMARY OF THE INVENTION

The primary advantage of this invention is to create a consistent therapeutic dose between 7-25(µl) in size. This invention resolves the issue of loss of medication mainly through tearing, which is a common problem associated with all eye drop dispensers for human or veterinary use.

One advantage of this invention is to tailor therapeutic response based on a variety of different size drops.

A second advantage of this invention is to produce more efficiency in medical eye drop delivery.

Another advantage of this invention is to decrease waste of costly medicine.

Yet another advantage to this invention is to enhance patient comfort i.e. less tearing from smaller drops.

Still another advantage of this invention is enhance patient compliance to Doctor recommended therapy through improved comfort and decreased cost.

Another advantage of this invention is to decrease doctor costs for dilating drops used in eye exams.

Yet another advantage to this invention is the simple design which defers the need for added instruction for use.

Still another advantage of this invention is the exceptional ease of adapting this technology to existing technology (i.e. the patient removes original bottle cap and screws new cap onto bottle with cannula tip.)

Another advantage of this invention results from applying cannula tip technology to a wide range of current dispenser types.

In accordance with the present invention, this new dispenser will produce smaller eye drops than current conventional standards. The smaller tip as described can be molded to any current eye drop dispensing tip or molded as part of a cap assembly that can be easily screwed onto an existing bottle or produced as part of the original eye bottle assembly. It will have dimensions consistent with current ophthalmic cannula technology (which is actually nothing more than an extension of current medical needle technology) in the range of 20-40 gauge depending on the size of drop desired and or needed.

For example, a 27 gauge cannula has a tip with an inner diameter of 0.017 inch and an outer diameter of 0.025 inch. This particular size cannula commonly used for intraocular surgery produces drops about 12.5 µl in size. Different sized cannula tips produce different size drops. However, since only 7-10 µl of any drop placed in the eye will actually remain, therapeutic response should not be lost in producing smaller drops. The present invention provides a consistent dose of medication. Consequently, a greater number of therapies can be generated from a fixed quantity of medicine and little to no additional patient instruction will be required in the use of this new dispenser type. Future experimentation may reveal that even smaller drops (i.e. 1-61 µl) may produce similar therapeutic efficacy.

BRIEF DESCRIPTION OF THE DRAWINGS

The accompanying drawings, which are incorporated in and form a part of this specification, illustrate embodiments of the invention and together with the description, serve to explain the principals of this invention.

FIG. 1 depicts an elevational side view of the preferred embodiment of the cannula tip eye drop dispenser device, constructed in accordance with the present invention;

FIG. 2 depicts a top view of the preferred embodiment of the cannula tip eye drop dispenser device, constructed in accordance with the present invention;

FIG. 3 depicts a bottom view of the preferred embodiment of the cannula tip eye drop dispenser device, constructed in accordance with the present invention;

FIG. 4 depicts an elevational cross-section view of the preferred embodiment of the cannula tip eye drop dispenser device, constructed in accordance with the present invention;

FIG. 5 depicts a top-oriented perspective view of the preferred embodiment of the cannula tip eye drop dispenser device, constructed in accordance with the present invention;

FIG. 6 depicts a bottom-oriented perspective view of the preferred embodiment of the cannula tip eye drop dispenser device, constructed in accordance with the present invention.

FIG. 13 depicts a side view of the application of an eye drop into the eye of a user with the preferred embodiment of the cannula tip eye drop dispenser device, constructed in accordance with the present invention;

Figure 11:
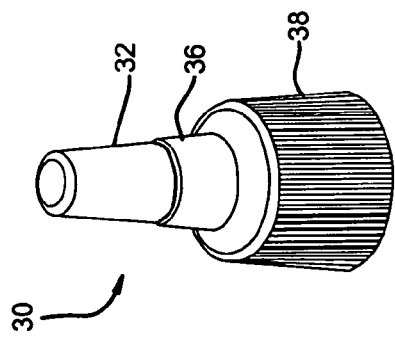
FIG. 11 depicts a top-oriented perspective view of an alternate embodiment of the cannula tip eye drop dispenser device including a cap assembly, constructed in accordance with the present invention.

For a fuller understanding of the nature and objects of the invention, reference should be had to the following detailed description taken in conjunction with the accompanying drawings which are incorporated in and form a part of this specification, illustrate embodiments of the invention and together with the description, serve to explain the principles of this invention.

DETAILED DESCRIPTION OF THE PREFERRED EMBODIMENT

Referring now to the drawings, wherein similar parts are identified by like reference numerals, FIG. 1 shows a perspective view of the preferred embodiment of the cannula tip eye drop dispenser 10 adapted for use with common ophthalmic medicines. Dispenser 10 includes a cannula tip 12 attached to an upper neck portion 16. Upper neck portion 16 is connected to a lower neck portion 18, which in turn is connected to a base 14. Base 14, lower neck portion 18, and upper neck portion 16 are preferably molded together, but can be joined in other manners, including removably, as would be recognized by one with ordinary skill in the art. Tip 12 has inner and outer dimensions such that drops as small as 5-10 μl can be produced. The current preferred embodiment is for tip 12 to be 1 mm to 2 mm in length with an inner dimension of 0.017 inches and outer diameter of 0.025 inches. These preferred dimensions will produce a drop roughly 12.5 μl in volume, which provides plenty of medication and allows for occasional drop-to-drop variability. It should be recognized however, that the dimensions of tip 12 can be altered to produce drops of different volumes for specific purposes. Preferably, dispenser 10 is comprised of thermoplastic material because of its durability and safety profile. However, dispenser 10 can be comprised of other types of plastic, or even certain types of metal.

Referring now to FIG. 2, there is shown a top view of dispenser 10. Particularly shown are the varying circumference sizes of dispenser 10 as well as the plurality of grip protrusions on base 14.

Referring now to FIG. 3, there is shown a bottom view of dispenser 10. Particularly shown is the relationship of the inner and outer diameter of base 14.

Referring now to FIG. 4, there is shown an elevational cross-section view of dispenser 10. This figure illustrates the threaded region 22 located on the interior portion of base 14.

Referring now to FIG. 5, there is shown a top-oriented perspective view of dispenser 10. Particularly shown is the spatial relationship between tip 12, upper neck portion 16, lower neck portion 18, and base 14.

Referring now to FIG. 6, there is shown a bottom-oriented perspective view of dispenser 10, illustrating threaded portion 22 located on the interior of base 14. Threaded portion 22 is designed to screw securely on most conventional eye drop dispensing bottles (see FIG. 14).

Figure 7:
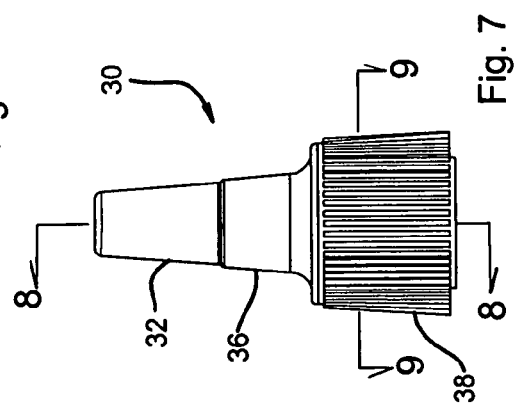
FIG. 7 depicts an elevational side view of an alternate embodiment of the cannula tip eye drop dispenser device including a cap assembly, constructed in accordance with the present invention.

Referring now to FIG. 7, there is shown an elevational side view of an alternate embodiment of the cannula tip eye drop dispenser device 30. Dispenser 30 includes a cap 32. Cap 32 serves to prevent leakage of eye drop solution when dispenser 30 is not in use. Cap 32 has an inner thread (not shown) that interlocks with a circumferential groove (not shown) in an upper neck portion 34. The interaction between the thread and groove allow cap 32 to lock into place and protect a tip 44 (see FIG. 8) when not in use. The inner thread of upper neck portion 34 is sized to come into contact with the outer edges of tip 44, such that, when the entire assembly is affixed to a common dispenser, the inner thread and tip 44 will come into contact. This contact creates new a reservoir for liquid, which will enhance drop formation and liquid flow. Cap 32 can vary in color to match industry standards based on class. For example, medical eye drops that function to pharmacologically dilate the pupil are dispensed with a red cap. Upper neck portion 34 is connected to a lower neck portion 36, which is attached to a base 38 (see FIG. 11). Base 38, lower neck portion 36, and upper neck portion 34 are preferably molded together, but can be joined in other manners, including removably, as would be recognized by one with ordinary skill in the art.

Figure 8:
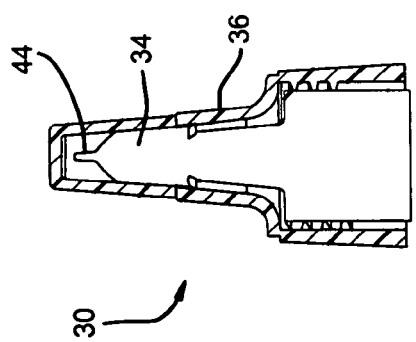
FIG. 8 depicts an elevational cross-section view of an alternate embodiment of the cannula tip eye drop dispenser device including a cap assembly, constructed in accordance with the present invention.

Referring now to FIG. 8, there is shown an elevational cross-section view of dispenser 30. As illustrated, upper neck portion 34 includes a tip 44 on the top portion thereof. Tip 44 has inner and outer dimensions such that drops as small as 5-10 μl can be produced. The current preferred embodiment is for tip 44 to be from 1 mm to 2 mm in length with an inner dimension of 0.017 inches and outer diameter of 0.025 inches. These preferred dimensions will produce a drop roughly 12.5 μl in volume, which provides plenty of medication and allows for occasional drop-to-drop variability. It should be recognized however, that the dimensions of tip 44 can be altered to produce drops of different volumes for specific purposes.

Figure 9:
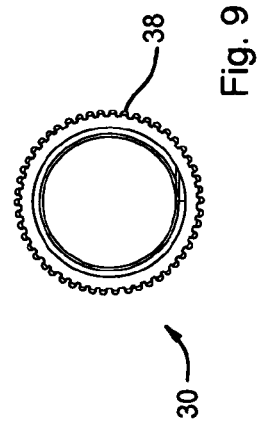
FIG. 9 depicts a bottom view of an alternate embodiment of the cannula tip eye drop dispenser device including a cap assembly, constructed in accordance with the present invention.

Referring now to FIG. 9, there is shown a bottom view of dispenser 30. Particularly shown is the relationship between the inner and outer diameter of base 38.

Figure 10:
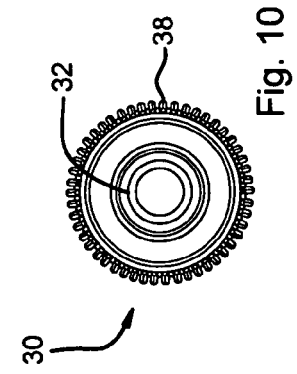
FIG. 10 depicts a top view of an alternate embodiment of the cannula tip eye drop dispenser device including a cap assembly, constructed in accordance with the present invention.

Referring now to FIG. 10, there is shown a top view of dispenser 30. Particularly shown are the varying circumference sizes of dispenser 30 as well as the plurality of grip protrusions on base 38.

Referring now to FIG. 11, there is shown a top-oriented perspective view of dispenser 30. Particularly shown is the spatial relationship between cap 32, lower neck portion 36, and base 38.

Figure 12:
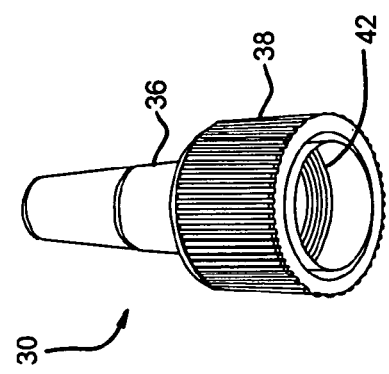
FIG. 12 depicts a bottom-oriented perspective view of an alternate embodiment of the cannula tip eye drop dispenser device including a cap assembly, constructed in accordance with the present invention.

Referring now to FIG. 12, there is shown a bottom-oriented perspective view of dispenser 30, illustrating threaded portion 42 located on the interior of base 38. Threaded portion 42 is designed to screw securely on most conventional eye drop dispensing bottles (see FIG. 14).

Referring now to FIG. 13, there is shown a side view of the application of an eye drop 66 into a user's eye 68 with dispenser 50. Dispenser 50 includes a cannula tip 52, an upper neck portion 54, a lower neck portion 56, a base 58, and a medicine bottle 62. During use of dispenser 50, a droplet 64 will first form to allow an operator to position dispenser 50 such that a later formed drop 66 will fall into a user's eye 68.

Figure 14:
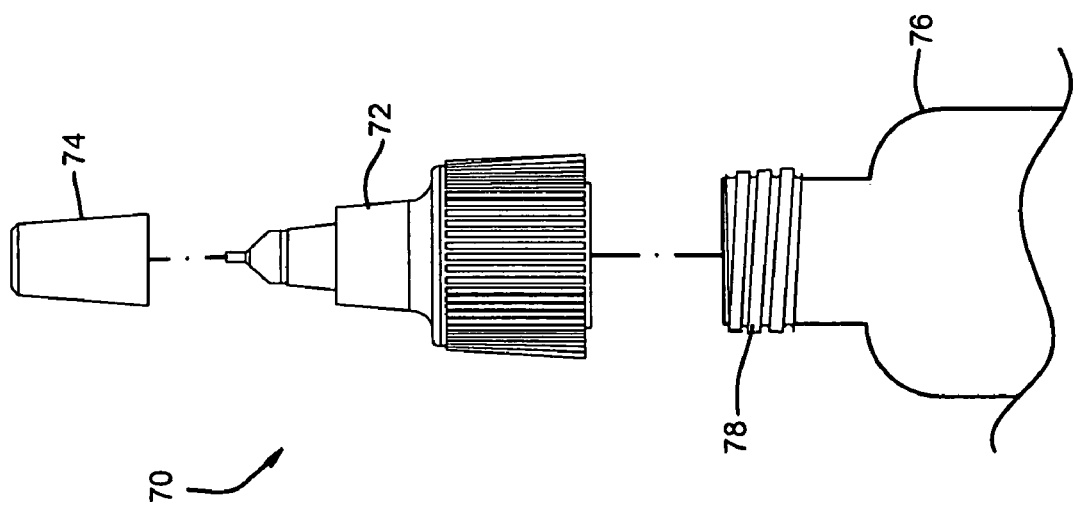
FIG. 14 depicts an exploded view of a cannula tip dispenser adapter, constructed in accordance with the present invention.

Referring now to FIG. 14, there is shown an exploded view of a cannula tip dispenser adapter 70. Adapter 70 includes a dispenser 72 and cap 74. Cap 74 is preferably secured to dispenser 72 by frictional attachment. A medicine bottle 76 contains bottle threads 78 to allow dispenser 72 to be securely attached to bottle 76 by use of a screwing motion. After dispenser 72 has been attached, cap 74 can be easily removed by applying a small amount of pulling force using the thumb and index finger of one hand. Bottle 76, with its new dispenser 72 attached, can be turned upside down over the eye (see FIG. 13). Bottle 76 is then gently squeezed to express a single drop from the tip onto the eye.

Figure 15:
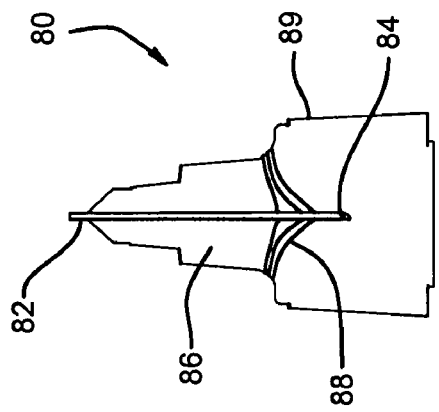
FIG. 15 depicts an elevational interior view of an alternate embodiment of a cannula tip dispenser device including a cap assembly, constructed in accordance with the present invention.

Referring now to FIG. 15, there is shown an elevational interior view of an alternate embodiment of a cannula tip dispenser device 80. Dispenser 80 includes a tip 82 extending from a neck portion 86 into a base 89. A hollow needle 84, as shown is connected to tip 82 and contained within neck portion 86 and base 89. This hollow needle has a sharp point on the end distal to the tip 82, as shown here in FIG. 15. Some medicine bottles (not shown) contain a diaphragm 88 at the top portion thereof to prevent the flow of medicine. When dispenser 80 is attached to a bottle, base 89 covers the top of the bottle region, including diaphragm 88, such that diaphragm 88 abuts neck portion 86 (as shown). When this occurs, dispenser 80 uses the sharp point on the distal end of hollow needle 84 to pierce diaphragm 88 and enter into base 89, thus allowing medicine to enter needle 84 from the bottle, pass through neck portion 86, and exit tip 82.

Figure 16:
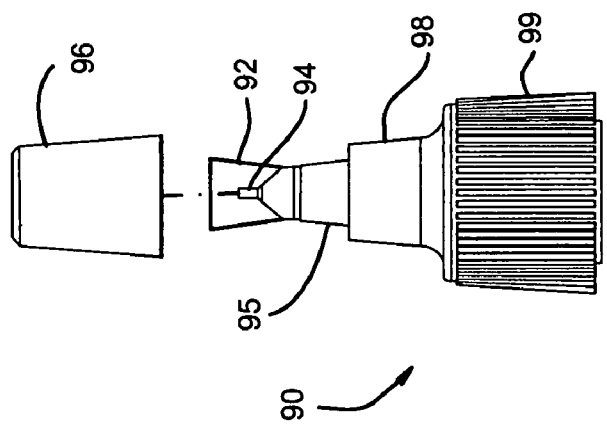
FIG. 16 depicts an elevational side view of a second alternate embodiment of the cannula tip eye drop dispenser device with the cap removed, constructed in accordance with the present invention.

Referring now to FIG. 16, there is shown an elevational side view of a second alternate embodiment of a cannula tip eye drop dispenser device 90. Dispenser 90 includes an eye protection cup 92 surrounding a cannula tip 94. Tip 94 is attached to an upper neck portion 95, which is attached to a lower neck portion 98. Lower neck portion 98 is attached to a base 99. Dispenser 90 has a removable cap 96 that attaches to lower neck portion 98, thus covering eye protection cup 92, tip 94, upper neck portion 95, and lower neck portion 98. Eye protection cup 92 is used to protect the eye of a user during the application of an eye drop into the user's eye.

Figure 17:
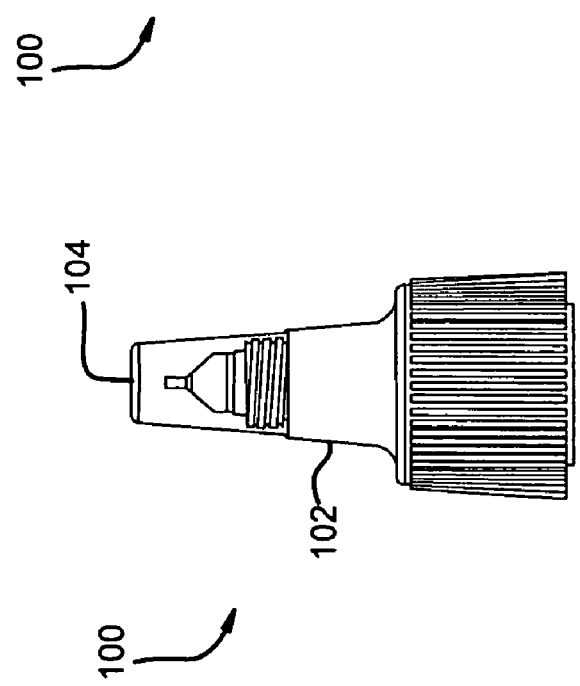
FIG. 17 depicts an elevational side view of a third alternate embodiment of the cannula tip eye drop dispenser device, constructed in accordance with the present invention.

Referring now to FIG. 17, there is shown an elevational side view of a third alternate embodiment of the cannula tip eye drop dispenser device 100. Dispenser 100 contains a cap 104 that secures to a neck portion 102 to cover the tip of dispenser 100. Cap 104 is threaded to provide secure attachment to neck portion 102.

Figure 18:
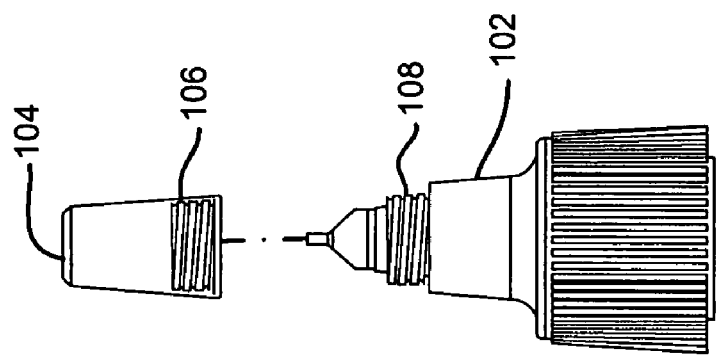
FIG. 18 depicts an elevational side view of a third alternate embodiment of the cannula tip eye drop dispenser device with the cap removed, constructed in accordance with the present invention.

Referring now to FIG. 18, there is shown an elevational side view of dispenser 100, with cap 104 removed. Depicted in the figure are cap threads 106 that align with dispenser neck threads 108 to form a secure attachment of cap 104 to neck portion 102.

Figure 19:
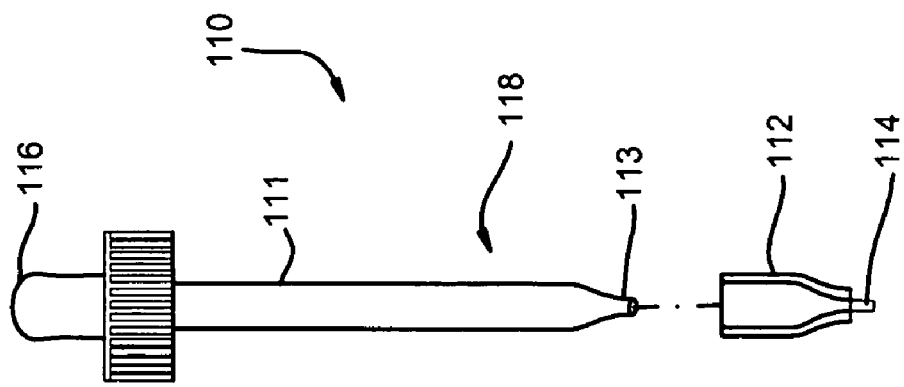
FIG. 19 depicts an elevational side view of a fourth alternate embodiment of the cannula tip eye drop dispenser device, constructed in accordance with the present invention.

Referring now to FIG. 19, there is shown an elevational side view of a fourth alternate embodiment of the cannula tip eye drop dispenser device 110. Dispenser device 110 utilizes a commonly used eye drop dispenser 111 that requires the user to squeeze a rubber top 116 to express a drop from its opening 113. The most common application for dispenser 111 is in an Eye Care Professional's office to dispense medication that can temporarily numb and stain the surface of the eye for about 10 minutes. However, this medication also causes discomfort from excessive tearing. These dye stained tears can stain skin for much longer than 10 minutes affecting patient appearance. The medication also can permanently stain clothing. Converting opening 113 to a cannula tip will produce drops 12.5 μl in size. These drops are small enough to reside in the eye with minimal to no tearing. Patient discomfort will be minimized and unsightly staining of skin and clothing avoided altogether without sacrificing patient evaluation. As such, dispenser 110 contains a cannula tip 114 contained within a tip dispenser adapter 112. Adapter 112 is preferably disposable and can be removably attached to cover opening 113.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The above description, together with the objects of the invention and the various features of novelty which characterize the invention, are pointed out with particularity in the claims annexed to and forming a part of this disclosure. For a better understanding of the invention, its operating advantages and the specific advantages attained by its uses, reference should be made to the accompanying drawings and descriptive matter in which there are illustrated preferred embodiments of the invention.

Furthermore, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

I claim:

1. An eye drop dispensing attachment comprising:
   a) a base portion, said base portion having an inner wall and an outer wall defining a circular base interior region, said base having a top end and a bottom end, said inner wall having a plurality of circumferential threads for rotatable attachment to a bottle;
   b) a lower neck portion connected to said top end, said lower neck portion having an inner wall and an outer wall defining a circular lower neck interior region having a smaller diameter than said base interior region, said lower neck portion having a lower neck top end and a lower neck bottom end;
   c) an upper neck portion connected to said lower neck top end, said upper neck portion having an inner wall and an outer wall defining a circular upper neck interior region having a smaller diameter than said lower neck interior region, said upper neck portion having an upper neck top end and an upper neck bottom end; and
   d) a tip connected to said upper neck top end, said tip being tubular in shape and having dimensions to produce liquid drops having between 5-12.5 micro-liters volume wherein said tip further includes a needle portion extending into said base interior region, said needle portion comprised of a hollow tube having a sharp point at the distal end thereof, whereby when the eye drop dispensing attachment is removably attached to a bottle containing liquid-resistant diaphragm barrier, said sharp point penetrates the diaphragm barrier and allows liquid from the bottle to flow through said needle portion to said tip whereby when the eye drop dispensing attachment is securely attached to a bottle containing liquid, a user inverts the bottle, causing liquid to enter said base portion, said lower neck portion, said upper neck portion, and said needle portion and said tip, wherein a drop of liquid of a specified volume forms around the outer opening of said tip, and a user can position said tip over a location where the drop is to be applied, such as an eye.

2. The eye drop dispensing attachment of claim 1 further comprising a cap for removable attachment to said upper neck portion and over said tip for the purpose of protecting said tip when the eye drop dispensing attachment is not in use.

3. The eye drop dispensing attachment of claim 2 wherein said cap is removably attached to said upper neck portion by frictional forces.

4. The eye drop dispensing attachment of claim 2 wherein said cap is removably attached to said upper neck portion by rotational movement, said upper neck portion having at least two threads for removable attachment to said cap and said cap having at least two threads on the interior portion thereof for removable attachment to said upper neck portion.

5. The eye drop dispensing attachment of claim 1, wherein the outer wall of said base portion contains a plurality of protrusions for the purpose of facilitating the rotatable attachment of the eye drop dispensing attachment onto a bottle.

6. The eye drop dispensing attachment of claim 1 further comprising a protective covering attached to said upper neck portion over said tip, whereby when a user positions said tip over a location where the drop is to be applied, such as an eye, said protective covering prevents the tip from coming into contact with a user's eye during use of the eye drop dispensing attachment.

7. The eye drop dispensing attachment of claim 1, wherein said base portion, said lower neck portion, said upper neck portion, and said tip are comprised of a thermoplastic material.

8. An eye drop dispensing device comprising:
a) a liquid reservoir portion, said liquid reservoir portion comprising a bottle; and
b) a liquid dispensing portion comprising:
  i) a base portion, said base portion having an inner wall and an outer wall defining a circular base interior region, said base portion having a top end and a bottom end,
  ii) a lower neck portion connected to said top end, said lower neck portion having an inner wall and an outer wall defining a circular lower neck interior region having a smaller diameter than said base interior region, said lower neck portion having a lower neck top end and a lower neck bottom end,
  iii) an upper neck portion connected to said lower neck top end, said upper neck portion having an inner wall and an outer wall defining a circular upper neck interior region having a smaller diameter than said lower neck interior region, said upper neck portion having an upper neck top end and an upper neck bottom end, and
  iv) a tip connected to said upper neck top end, said tip being tubular in shape and having dimensions to produce liquid drops having between 5-12.5 micro-liters volume wherein said tip further includes a needle portion extending into said base interior region, said needle portion comprised of a hollow tube having a sharp point at the distal end thereof, whereby when the eye drop dispensing attachment is removably attached to a bottle containing a liquid-resistant diaphragm barrier, said sharp point penetrates the diaphragm barrier and allows liquid from the bottle to flow through said needle portion to said tip whereby when the liquid reservoir portion contains a liquid, a user inverts the bottle, causing the liquid to enter said base portion, said lower neck portion, said upper neck portion, and said tip, wherein a drop of liquid of a specified volume forms around the outer opening of said tip, and a user can position said tip over a location where the drop is to be applied, such as an eye.

9. The eye drop dispensing device of claim 8 further comprising a protective covering coupled to said upper neck portion over said tip, whereby when a user positions said tip over a location where the drop is to be applied, such as an eye, said protective covering prevents the tip from coming into contact with a user's eye during use of the eye drop dispensing device.

10. The eye drop dispensing device of claim 8 further comprising a cap for removable attachment to said upper neck portion and over said tip for the purpose of protecting said tip when the eye drop dispensing device is not in use.

11. The eye drop dispensing attachment of claim 10 wherein said cap is removably attached to said upper neck portion by frictional forces.

12. The eye drop dispensing attachment of claim 10 wherein said cap is removably attached to said upper neck portion by rotational movement, said upper neck portion having at least two threads for removable attachment to said cap and said cap having at least two threads on the interior portion thereof for removable attachment to said upper neck portion.

* * * * *